United States Patent [19]
Barkley et al.

[11] Patent Number: 6,064,909
[45] Date of Patent: May 16, 2000

[54] WATER RESISTANT SPEAKER PORT FOR AUTOMATED EXTERNAL DEFIBRILLATORS

[75] Inventors: Steven D. Barkley, Champlin; Robert K. Johnson, Blaine; Nora J. Utke, Minneapolis, all of Minn.

[73] Assignee: SurVivaLink Corporation, Minneapolis, Minn.

[21] Appl. No.: 09/056,957

[22] Filed: Apr. 8, 1998

Related U.S. Application Data

[60] Provisional application No. 60/041,868, Apr. 8, 1997.

[51] Int. Cl.$^7$ ........................................................ A61N 1/39
[52] U.S. Cl. .................................................. 607/5; 607/36
[58] Field of Search .................................. 607/2, 1, 5, 36, 607/63; 600/523, 524, 528; 381/355, 361, 386, 189

[56] References Cited

U.S. PATENT DOCUMENTS

| | | |
|---|---|---|
| 4,610,254 | 9/1986 | Morgan et al. . |
| 5,333,616 | 8/1994 | Mills et al. ............................... 600/508 |
| 5,464,428 | 11/1995 | Hill . |
| 5,683,423 | 11/1997 | Post . |
| 5,700,281 | 12/1997 | Brewer et al. ............................... 607/5 |

*Primary Examiner*—Kennedy J. Schaetzle
*Attorney, Agent, or Firm*—Patterson & Keough, P.A.

[57] ABSTRACT

An automated external defibrillator (AED) having a housing and an openable lid with a water resistant speaker port formed in the housing below the openable lid. A water resistant fabric is attached underneath the speaker port to resist water passing into the interior of the AED while allowing clear sound output from the speaker located beneath the speaker port. A microphone is positioned adjacent to the speaker port in the AED for recording emergency scene ambient activities. This position uses the existing water resistant opening thereby taking advantage of the good sound transmitting properties of the opening for recording purposes and at the same time eliminating the need for an additional cavity in the housing where water could ingress. Positioning the microphone near the speaker also eliminates the need for an additional wiring harness.

2 Claims, 5 Drawing Sheets

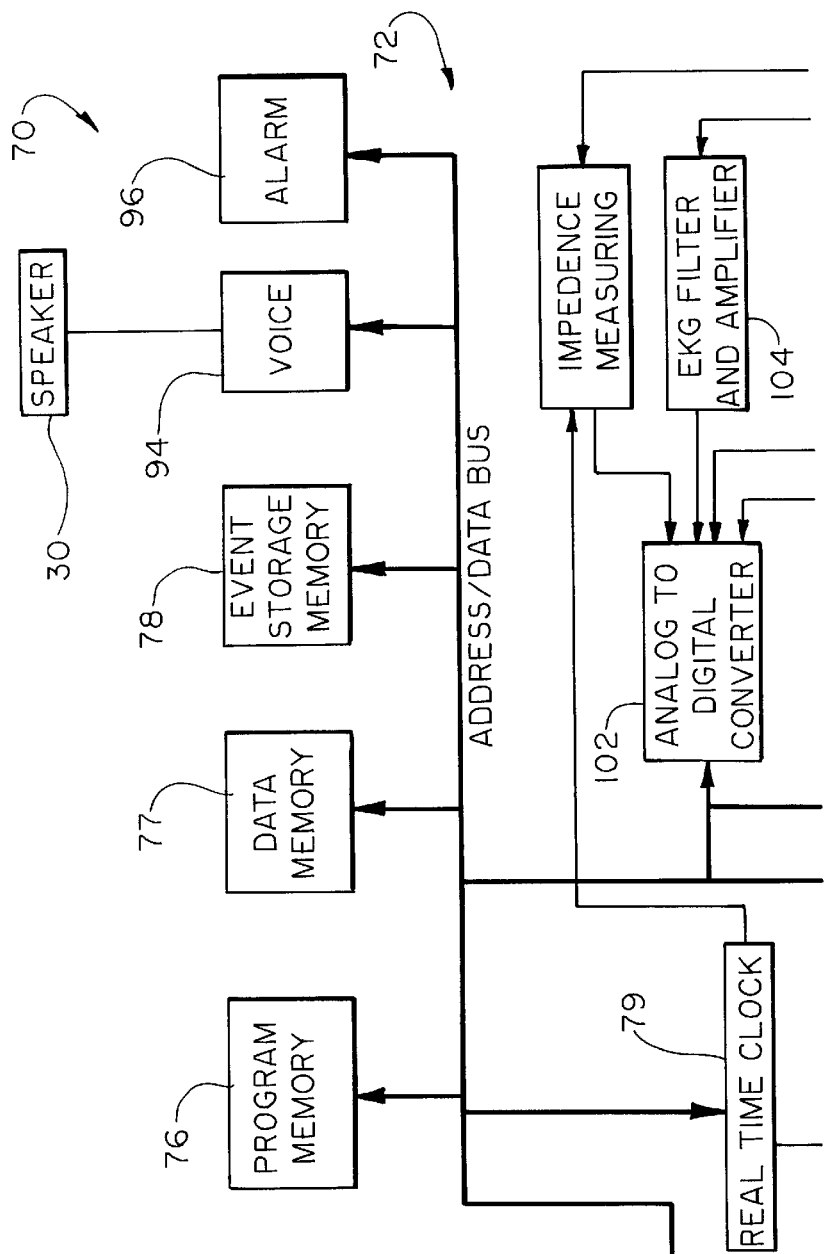
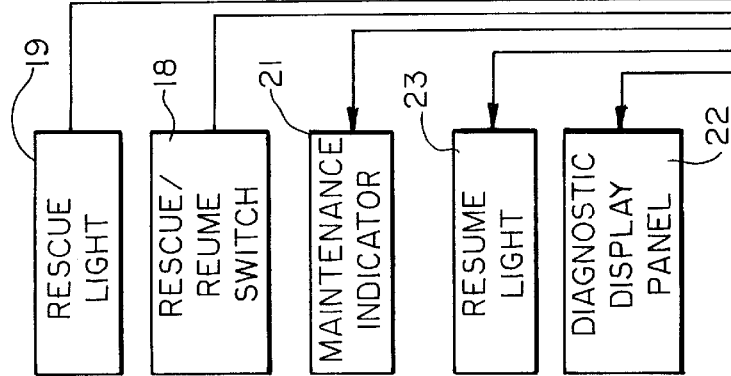
Fig. 2
| FIG. 2a | FIG. 2b |
Fig. 2a

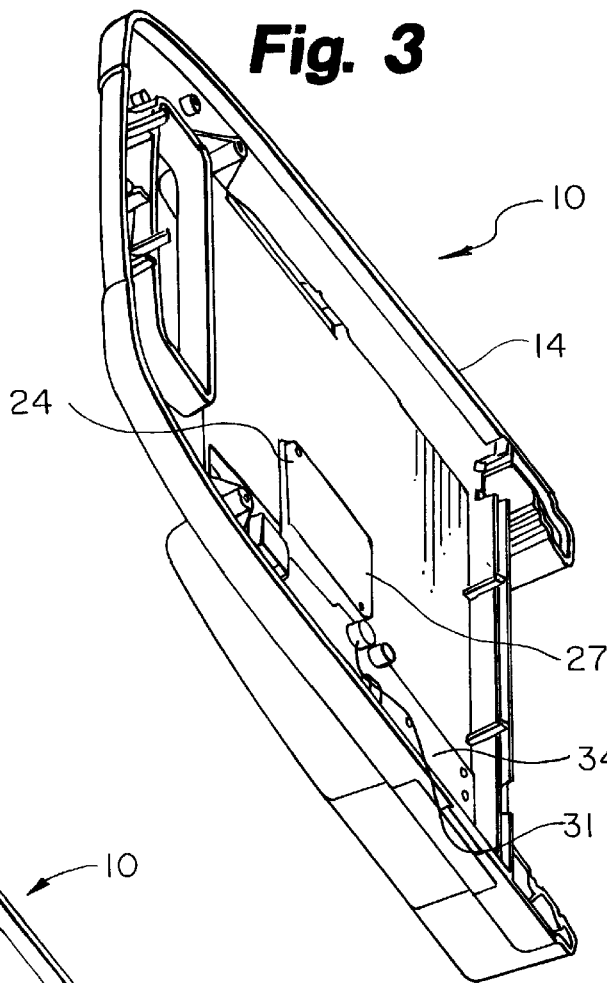
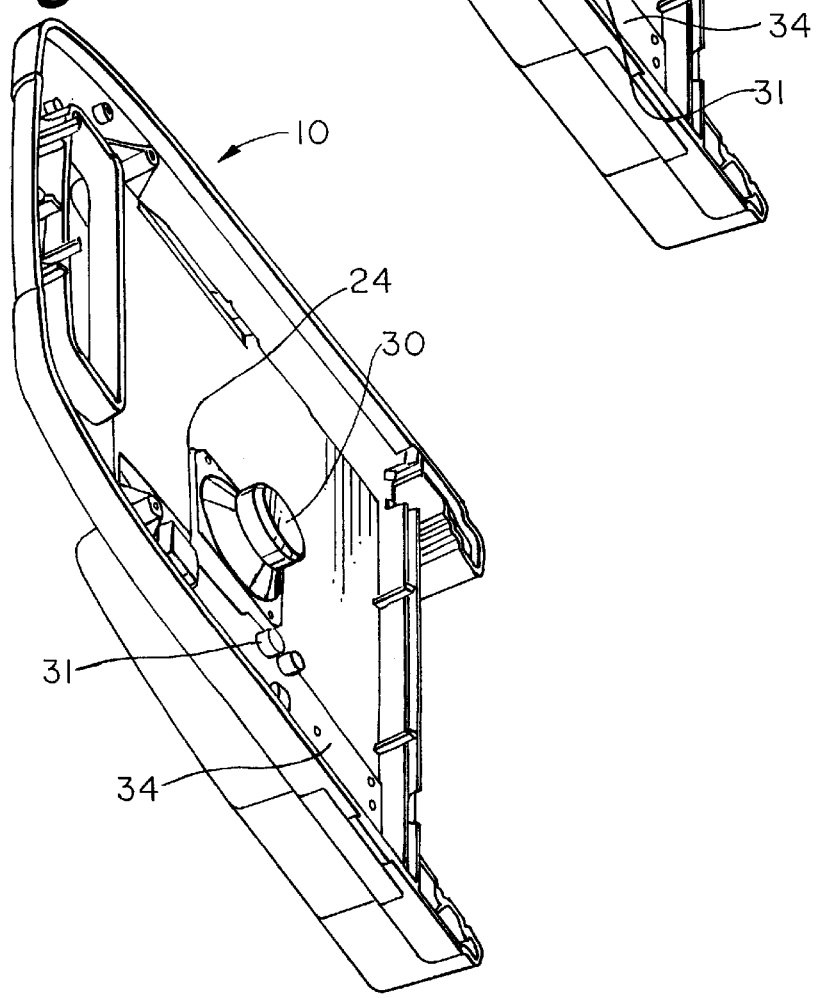

WATER RESISTANT SPEAKER PORT FOR AUTOMATED EXTERNAL DEFIBRILLATORS

RELATED APPLICATIONS

The present invention is related to U.S. Provisional Patent Application Ser. No. 60/041,868, filed Apr. 8, 1997, entitled Water Resistant Speaker Port For Automated External Defibrillators, the content of which is herein incorporated by reference, and priority to which is claimed according to 35 U.S.C. § 119(e).

FIELD OF THE INVENTION

The present invention is an automated external defibrillator (AED) having a water resistant speaker port. In particular, the present invention provides a water resistant fabric attached underneath a speaker port to prevent water from ingressing into the interior of an AED. Another feature of the present invention is the positioning of a microphone adjacent to the speaker port to eliminate the need for an additional cavity in the housing where water could ingress.

BACKGROUND OF THE INVENTION

Cardiac arrest, exposure to high voltage power lines, and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is unconscious.

Automated external defibrillators (AEDs) are used by first-responders, emergency medical technicians and other trained personnel to resuscitate patients in cardiac fibrillation. The American Heart Association has identified early defibrillation as the key link in the Chain of Survival from sudden cardiac arrest. Therefore, it is important that AEDs be ready for use on a moment's notice and that they be simple to use.

To help ensure a high level of confidence that they will be operational when needed, AEDs perform self tests to check for the presence and connection of defibrillator electrodes, battery charger state, the function of the high voltage circuit, and the function of the digital control system. If maintenance is needed, audio alarms and visual signals are given. To ensure the AED is fast and easy to use, it gives voice prompts to guide the user through the approved cardiac resuscitation process step by step. AEDs use built-in speakers to sound these audible alarms and voice prompts.

AEDs are used anywhere an emergency occurs, therefore, indoor and outdoor operation is important. Outdoor use requires that openings in the AED housing be substantially water resistant to prevent damage to internal electrical components due to water contact. However, current methods for weatherproofing speaker openings in AEDs may reduce speaker output quality, which in turn makes current AEDs sound like computers. This is undesirable in the high stress atmosphere of a cardiac arrest rescue, where a human-like voice giving instructions would be more clear, understandable, soothing, and calming to the person performing the intense life saving procedure.

Data collected on response time and activities at the emergency scene can be useful for analyzing a number of critical aspects of patient resuscitation. These include evaluating response procedures, training responders using real-life scenarios, and evaluating patient response to known treatment. It would be desirable to provide an AED capable of recording activities at the emergency scene for later use. Furthermore, it would be desirable to provide an AED that would clearly record ambient activities in all environmental conditions.

SUMMARY OF THE INVENTION

In accordance with the present invention, an automated external defibrillator (AED) having a water resistant speaker port is provided that overcomes the disadvantages and shortcomings of the prior art. Specifically, an AED is provided having a housing and an openable lid. A speaker port is formed in the housing below the openable lid. A water resistant fabric is attached underneath the speaker port to resist water passing into the interior of the AED while allowing clear sound output from the speaker positioned below the speaker port.

In accordance with one aspect of the present invention, a microphone is provided for recording emergency scene ambient activities. More specifically, the microphone is positioned adjacent to the speaker port. This position uses the existing water resistant speaker port thereby taking advantage of the good sound transmitting properties of the opening for recording purposes and at the same time eliminating the need for an additional cavity in the housing where water could ingress. Positioning the microphone near the speaker also eliminates the need for an additional wiring harness.

BRIEF DESCRIPTION OF THE DRAWINGS

FIG. 3 is a cut away of the AED of FIG. 1 illustrating the underside of the top half of the housing with a water resistant fabric according to the present invention attached.

FIG. 4 is a perspective view of the underside of the top half of the AED housing of FIG. 3 with a speaker attached.

DETAILED DESCRIPTION OF THE PREFERRED EMBODIMENTS

Figure 1:
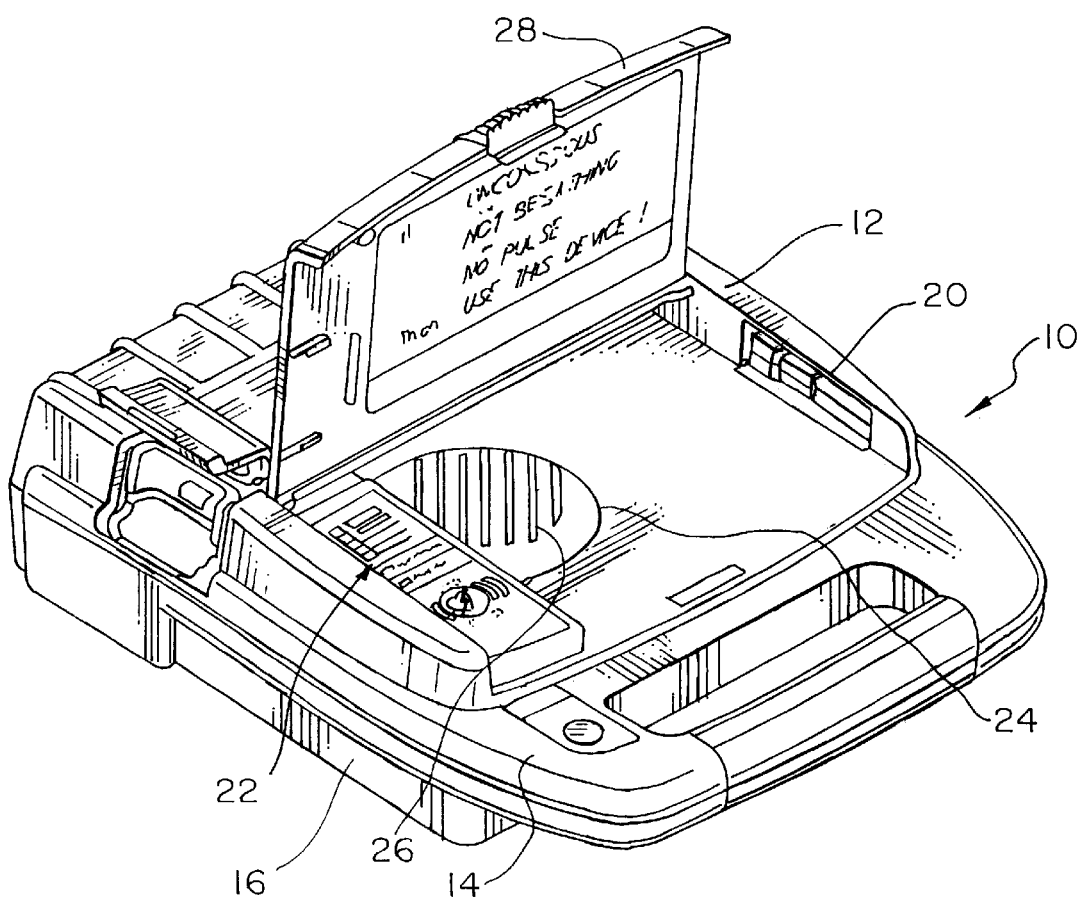
FIG. 1 is a perspective view of an automated external defibrillator (AED) having a top and bottom half and a lid opened.

The present invention is a water resistant speaker port for automated external defibrillators (AEDs). An AED 10 in accordance with the present invention is illustrated generally in FIG. 1. As shown, AED 10 includes a housing 12 with upper and lower portions 14 and 16, respectively. An openable lid 28 is also provided and is illustrated in an open position. Underneath openable lid 28 is an electrode connector port 20, a diagnostic panel 22 and a speaker port 24. As can be seen, speaker port 24 is comprised of a series of slots 26 which allow gas, liquid, and sound to pass through housing 12. It is very important that water be kept out of housing 12. If water were to get into housing 12, the electrical components inside of AED 10 could be shorted out.

Figure 2B:
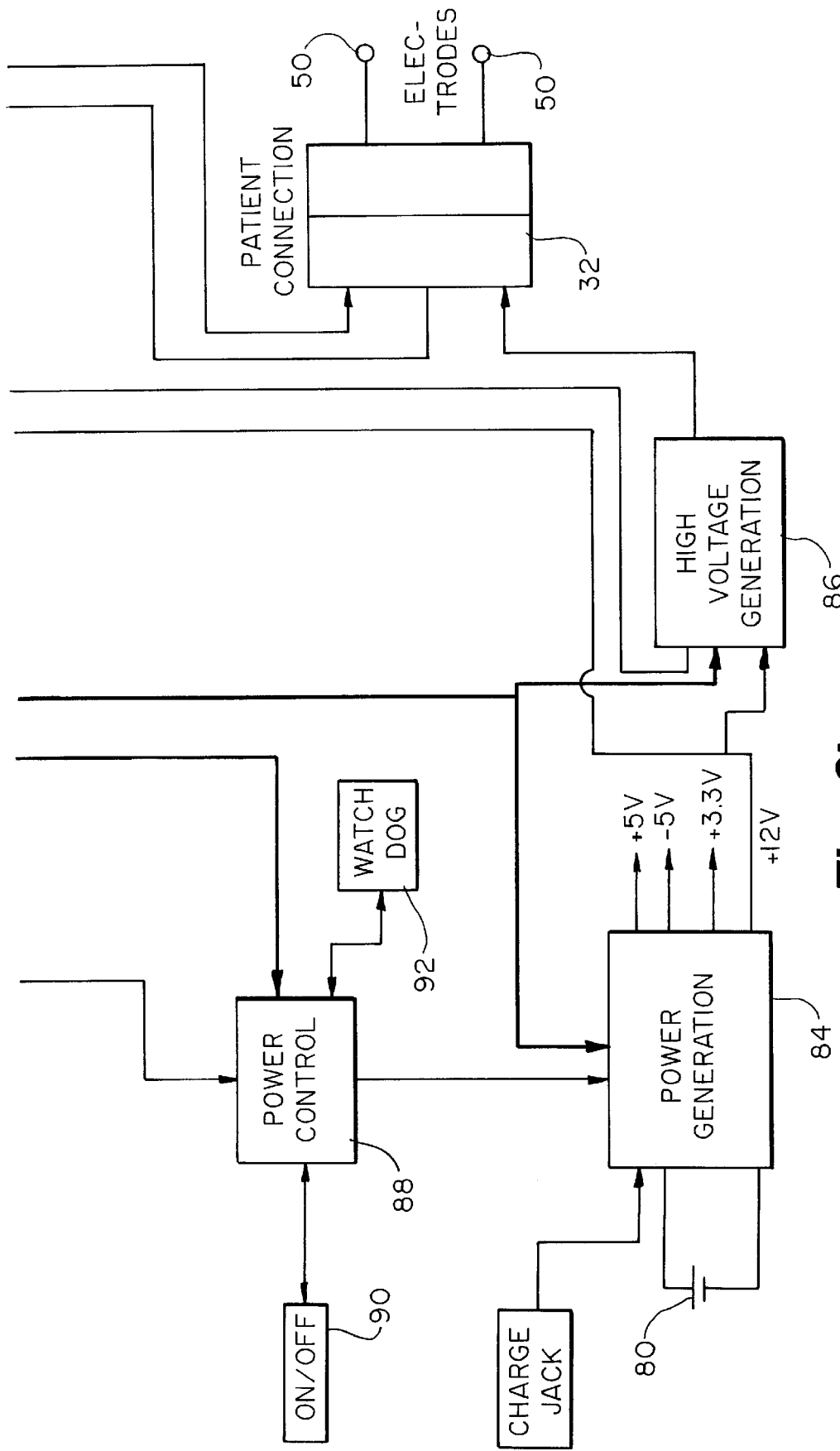
FIG. 2 is a block diagram of the electrical system of the AED shown in FIG. 1.

FIG. 2 is a block diagram of the electrical system 70 of AED 10. The overall operation of AED 10 is controlled by a digital microprocessor-based control system 72 which includes a processor 74 interfaced to program memory 76, data memory 77, event memory 78 and real time clock 79. The operating program executed by processor 74 is stored in program memory 76. Data memory 77 is used by processor 74 as a scratch pad memory during the execution of the operating program. Electrical power is preferably provided by a plurality of lithium sulfur dioxide battery cells 80 provide primary voltages of 11.6 volts (+12V) and 5.4 volts (+5V), and which are removably positioned within the battery compartment and connected to power generation circuit 84.

Power generation circuit 84 is also connected to power control circuit 88 and processor 74. Power control circuit 88 is connected to lid switch 90, watch dog timer 92, real time clock 79 and processor 74. Lid switch 90 is a preferably a hall effect switch and provides signals to processor 74 indicating whether lid 28 is open or closed. It should be noted that other switches, such as magnetic reed relay switches may also be used. Rescue/resume switch 18, maintenance indicator 21, rescue light 19, resume light 23, indicator lights on diagnostic display panel 22, voice circuit 94 and piezoelectric audible alarm 96 are also connected to processor 74. Voice circuit 94 is connected to the speaker 30. In response to voice prompt control signals from processor 74, circuit 94 and speaker 30 generate the audible voice prompts described below.

High voltage generation circuit 86 is also connected to and controlled by processor 74. In response to charge control signals provided by processor 74, high voltage generation circuit 86 is operated in a charge mode during which one set of semiconductor switches (not separately shown) cause a plurality of capacitors (also not shown), to be charged in parallel with the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to the high voltage generation circuit 86.

AED 10 also includes electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of AED 10 is initiated when an operator opens lid 28 to access a packaged pair (not shown) of electrodes 50. The opening of the lid 28 is detected by lid switch 90, which effectively functions as an on/off switch. In response to this action, power control circuit 88 activates power generation circuit 84 and initiates rescue mode operation of processor 74. Processor 74 then begins its rescue mode operation by switching maintenance indicator 21 to a maintenance required state (e.g., a red visual display in one embodiment), flashing rescue light 19 and the indicator lights on diagnostic display panel 22, and performing a lid opened self-test.

During the lid opened self-test, processor 74 checks: 1) the charge state of battery 80; 2) the interconnection and operability of electrodes 50; 3) the state of event memory 78; 4) the functionality of real time clock 79; and 5) the functionality of A/D converter 102. Processor 74 accesses the event memory 78 to determine whether data from a previous rescue is still stored in the memory. If so, processor 74 causes light 49 on diagnostic panel 22 to be illuminated, and initiates the generation of a "Press resume button to clear memory and continue." voice prompt. If rescue/resume switch 18 is pressed by the operator following the activation of these indicators, processor 74 clears event memory 78 and proceeds with its rescue mode operation. The "service" light on diagnostic display panel 22 is illuminated by processor 74 if faults are identified in either of real time clock 79 or converter 102.

If the lid opened self-test is successfully completed, processor 74 switches maintenance indicator 21 to an operational state (e.g., a green color in one embodiment), and initiates the generation of an audible "Place electrodes." voice prompt. While the user places the electrodes, processor 74 monitors the impedance signals received through A/D converter 102 to determine whether the impedance across the electrodes indicates that they have been properly positioned on the patient. If the correct impedance is not measured, processor 74 initiates the generation of a "Check electrodes." voice prompt.

After detecting an impedance indicating the proper placement of electrodes 50, and without further action by the operator (i.e., automatically), processor 74 begins a first analyze sequence by initiating the generation of a "Do not touch patient. Analyzing rhythm." voice prompt, and analyzing the patient's cardiac rhythm. If processor 74 determines that the patient has a non-shockable cardiac rhythm that is not susceptible to treatment by defibrillation pulses (e.g., no pulse rather than a fibrillating rhythm), it initiates the generation of a "Check pulse. If no pulse, give CPR." voice prompt. One minute after this voice prompt, processor 74 repeats the initiation of the "Do not touch patient. Analyzing rhythm." voice prompt and the associated cardiac rhythm analysis.

When a shockable cardiac rhythm is detected, processor 74 begins a first charge sequence by initiating the generation of a "Charging." voice prompt, and causes high voltage generation circuit 86 to operate in the charge mode. When high voltage generation circuit 86 is charged, processor 74 begins a first shock sequence by initiating the generation of a "Stand clear. Push flashing button to rescue." voice prompt, and the flashing illumination of rescue light 19. The operator actuation of rescue/resume switch 18 will then cause processor 74 to operate high voltage generation circuit 86 in the discharge mode, and results in the application of a defibrillation pulse to the patient to complete the first series of analyze/charge/shock sequences.

Following the first series of analyze/charge/shock sequences, processor 74 times out a short pause of about five seconds to allow the heart to reestablish its cardiac rhythm before beginning a second series of analyze/charge/shock sequences. The second series of analyze/charge/shock sequences is identical to the first series described above, except the energy content of the defibrillation pulse can be different. If the second series of analyze/charge/shock sequences ends with the delivery of a defibrillation pulse, processor 74 again times out a short pause of about five seconds before beginning a third analyze/charge/shock sequence. The third series is also identical to the first series, but processor 74 controls high voltage generation circuit 86 in such a manner as to cause the defibrillation pulse delivered upon the actuation of rescue/resume switch 18 to have a larger energy content.

Following the delivery of a defibrillation pulse at the end of the third series of analyze/charge/shock sequences, or after identifying a non-shockable cardiac rhythm, processor 74 initiates the generation of a "Check Pulse. If no pulse, give CPR." voice prompt. Processor 74 then times a one minute CPR period to complete a first set of three series of analyze/charge/shock sequences. Rescue mode operation then continues with additional sets of three series of analyze/charge/shock sequences of the type described above. Processor 74 ends rescue mode operation of AED 10 when a preset number of analyze/charge/shock sequences have been performed, or lid 28 is closed. The maximum number of shocks per rescue can be set to any value between 6 and 255.

FIG. 3 illustrates a cut away of AED 10 showing the underside of upper portion 14 of housing 12. As can be seen in FIG. 3, a water resistant material 27 is provided covering speaker port 24. In the preferred embodiment of the present invention, the water resistant material is made from microporous polytetrafluoroethylene. A common brand of this material is Goretex® made by W. L. Gore and Associates. This material allows diffusion of air and water vapor but prevents liquid ingress. The material also transmits sound with insignificant distortion. It should be noted that other water resistant materials could also be used without departing from the spirit or scope of the present invention. Another such material is fabric made from non-woven polyester fibers and treated to resist water. This material is commercially available from W. L. Gore & Associates (Model #GAWV-7).

Figure 5:
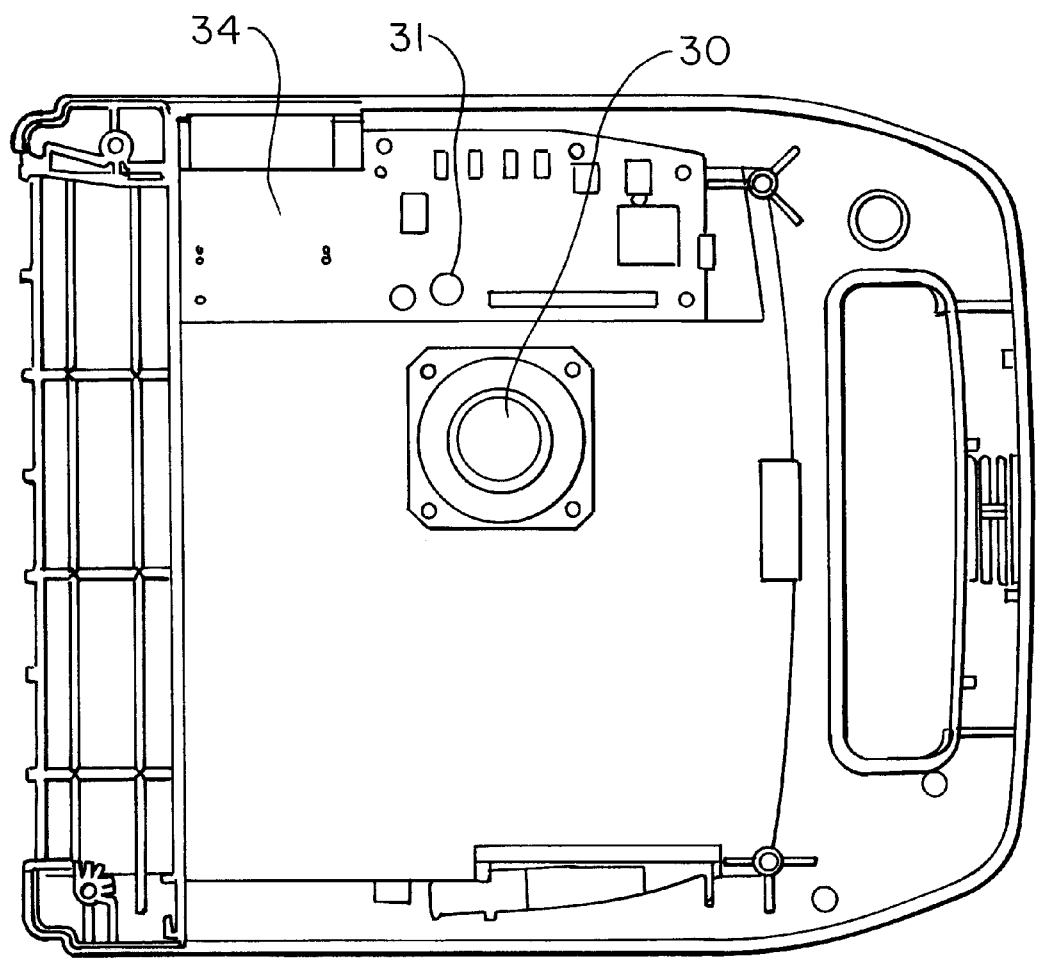
FIG. 5 is a top plan view of the underside of the top half of the AED of FIG. 3 illustrating the positioning of a microphone adjacent the speaker.

FIGS. 4 and 5 illustrate the cut away of FIG. 3 with speaker 30 mounted to the underside of speaker port 24. FIGS. 4 and 5 also illustrate a microphone 31 positioned adjacent to speaker 30 on a circuitboard 34. Not only does speaker 30 amplify sound, it also allows sound to pass through it with little distortion to reach microphone 31. Microphone 31 is provided to record sound in the vicinity of the rescue. The information recorded from the rescue scene can be used to analyze many aspects of patient resuscitation, including response procedures, response personnel training, response timing, treatment methods, and patient reaction. In AED 10, up to 20 minutes of sound may be recorded.

By placing microphone 31 on circuitboard 34 adjacent to speaker 30, the need for an additional hole in housing 12 is eliminated, thereby eliminating another potential liquid ingress point. This location provides good sound quality also because water resistant material 27 and speaker 30 allow sound to pass with insignificant distortion. Also, because microphone 31 is mounted directly to circuitboard 34, there is no need for an additional wiring harness. Direct mounting reduces material costs, avoids additional assembly steps, and makes the microphone more reliable since there are fewer moving parts subject to failure due to wear.

Although the present invention has been described with reference to preferred embodiments, those skilled in the art will recognize that changes can be made in form and detail without departing from the spirit and scope of the invention.

What is claimed is:

1. An automated external defibrillator (AED) comprising:

an AED housing;

a speaker port formed in the housing;

a microphone positioned in the AED housing adjacent the speaker port; and a layer of water resistant material mounted to the housing covering the speaker port.

2. An automated external defibrillator (AED) comprising:

an AED housing absent a microphone port, having an interior and an exterior;

an openable lid attached to the housing;

a port formed in the housing beneath the openable lid;

a layer of water resistant material mounted to the housing covering the port;

a microphone positioned in the interior of the housing adjacent the port; and a speaker positioned under the port wherein the speaker produces sound and allows sound to pass into the housing to the microphone.

\* \* \* \* \*